United States Patent [19]
Chalifoux

[11] Patent Number: 5,336,092
[45] Date of Patent: * Aug. 9, 1994

[54] DENTAL POST CONSTRUCTION

[75] Inventor: Paul R. Chalifoux, Wellesley, Mass.

[73] Assignee: Wellesley Research Associates, Inc., Wellesley, Mass.

[*] Notice: The portion of the term of this patent subsequent to May 31, 2011 has been disclaimed.

[21] Appl. No.: 969,060

[22] Filed: Oct. 30, 1992

Related U.S. Application Data

[63] Continuation-in-part of Ser. No. 908,366, Jul. 6, 1992, which is a continuation-in-part of Ser. No. 896,388, Jun. 10, 1992, which is a continuation-in-part of Ser. No. 739,670, Aug. 3, 1991, Pat. No. 5,277,583.

[51] Int. Cl.⁵ ............................................. A61C 5/08
[52] U.S. Cl. .................................................... 433/220
[58] Field of Search ................. 433/76, 165, 166, 220, 433/221

[56] References Cited

U.S. PATENT DOCUMENTS

| | | | |
|---|---|---|---|
| 626,738 | 6/1899 | Underwood | 433/221 |
| 1,218,289 | 3/1917 | Maker | 433/220 |
| 1,228,488 | 6/1917 | Shaw | 433/221 |
| 1,517,500 | 12/1924 | Fredericks | 433/221 |

FOREIGN PATENT DOCUMENTS 844341  7/1952  Fed. Rep. of Germany ...... 433/220

*Primary Examiner*—John J. Wilson
*Attorney, Agent, or Firm*—Paul J. Cook

[57] ABSTRACT

A dental post is provided including a stem and a flange secured to an intermediate vertical position on said stem to delineate a top stem section and a bottom stem section. A support can be positioned to connect the flange with the top stem section. The flange can be provided with through holes or pins formed integrally therewith.

13 Claims, 4 Drawing Sheets

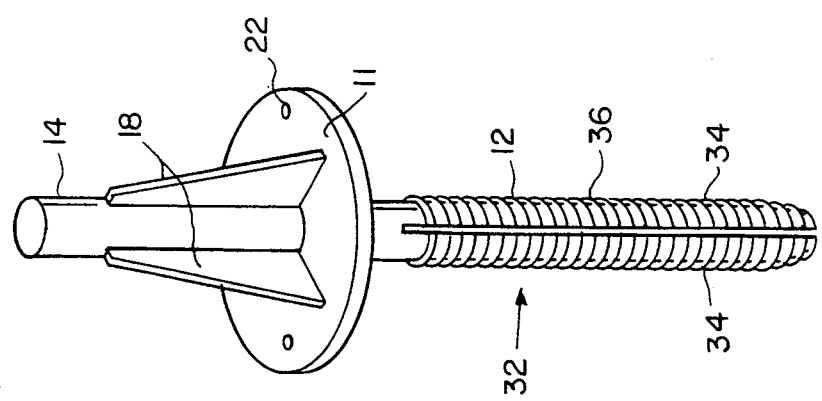
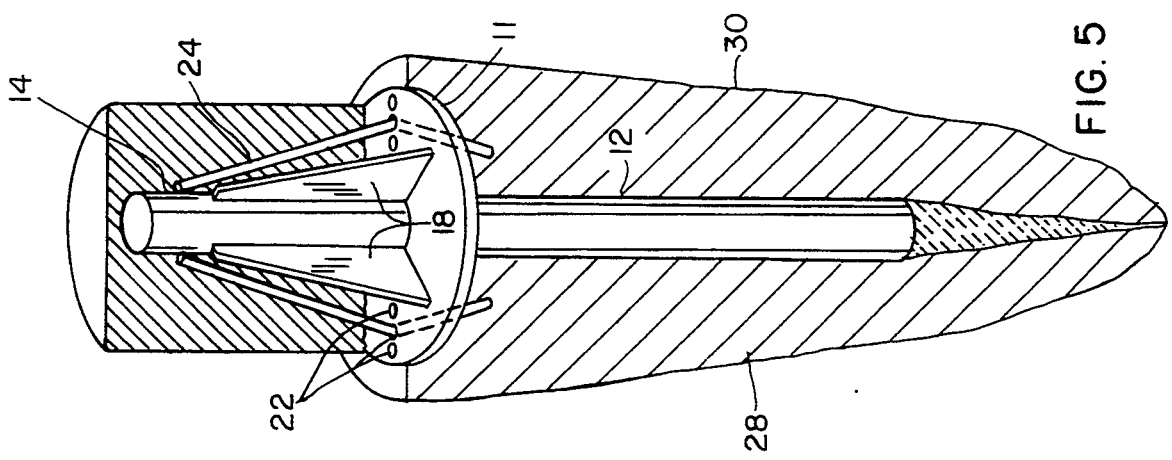
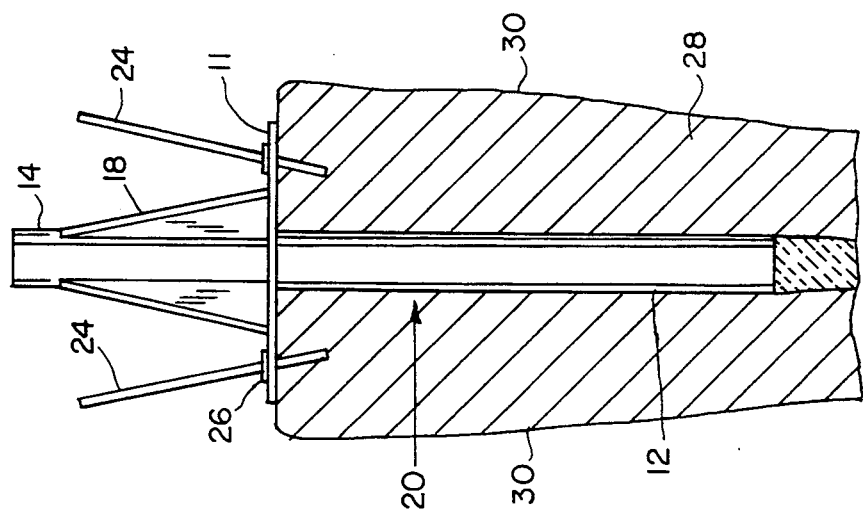

DENTAL POST CONSTRUCTION

REFERENCE TO RELATED APPLICATION

This application is a continuation-in-part of Ser. No. 07/908,366, filed Jul. 6, 1992 which, in turn, continuation-in-part of Ser. No. 07/896,388, filed Jun. 10, 1992 which, in turn, is a continuation-in-part of application Ser. No. 07/739,670 filed Aug. 3, 1991, now U.S. Pat. No. 5,277,583.

BACKGROUND OF THE INVENTION

This invention relates to a dental post construction which can be inserted into a tooth stub and which is utilized to improve retention of a dental restoration built onto the tooth stub.

It is present dental procedure to form a dental prosthetic structure onto a tooth stub for replacement of missing dentition. In this procedure, a tooth stub is initially prepared by removing the diseased or damaged top portion of a tooth to form a tooth stub. A base is formed by drilling into the root canal portion of the tooth stub to form a space into which a dental post can be inserted. Presently available dental post include grooves on their surface designed to improve retention of the post within the tooth stub. Dental cement is employed in the bore in conjunction with the dental post to secure the post in the tooth stub. A portion of the post extends above the tooth stub upper surface so that a dental prosthesis formed on the tooth stub can be retained. Presently, the implantation of a dental post relies either upon the adherent strength of an adhesive or on lateral stress forces between the dental post and the canal wall of screw type posts.

Preformed posts are posts which are premade to specific dimensions with matching burs having cutting surfaces. The burs have a matching diameter to the post and prepare the root to accept a post. A post is then tried in the root and cut to the appropriate length. Cement is spun into the canal with a device referred to as a lenticulo spiral, placed directly with a syringe and/or placed directly on the post. The post is placed in the canal and held in position until excess cement extrudes and the cement hardens. Most preformed posts require placing filling material around the top of the post to transfer strength from the post to the crown. This procedure is referred to as the core build up or post and core procedure.

There are many problems which are encountered when utilizing preformed posts. These include:

An inaccurate fit develops with present bur technology.

Potential for perforation of the root is great with present burs.

There is inadequate resistance to rotational forces on the post.

Root fracture caused by lateral stresses occurs.

There is weak transfer of strength from the post to the crown positioned on the post.

An accurately drilled hole results in good proximity of the post to the canal walls with a thin cement layer to provide greater success in properly positioning the post. The hole is inaccurate if tipping or vibrating of the bur occurs during root preparation as occurs with present drilling systems. This adds to the failure rate of preformed post systems. Drilling a straight hole for a straight post in a curved canal or drilling a hole which does not align with a canal can lead to perforation of a root and loss of a tooth. All posts must resist normal rotational forces which occur during normal or abnormal functions if there is not sufficient tooth structure to provide resistance. In general, preformed posts do not provide good stability against rotational force because they are round and rotate easily when placed in a round hole such as that provided by present bur systems. Presently, to compensate for this, a separate pin may be placed into the tooth, however, screw pins increase the likelihood of root fracture. Some systems try to make posts oval or non-symmetrical at the top but do not supply dependable resistance and retention form. Cement merely provides suction to hold a post in position. The strength of the cement becomes a weak point to the root-post-crown relationship. Constant repeated forces of chewing causes potential breakdown on the tooth-cement-crown interface with subsequent cement wash out and crown post failure. An uneven or excessive amount of force can cause root fracture and tooth loss. Screw type posts can exert large lateral stresses which leads to potential root fracture and tooth loss. In addition, forceful placement of cement type posts without proper venting of cement can cause root fracture and tooth loss. Filling material is placed around a preformed post above the root to accept a crown after the post is cemented. The strength and long term stability of this material becomes a weak link in long term success of the crown. In addition, proper design of the post above the root is critical to resist rotation or dislodging of the filling material from the post.

A cast post is inducted for root canalled teeth with no clinical crown (no tooth above the height of the gums) and/or teeth with root canal spaces which are shaped in such a manner that a preformed post can not fit properly. For example, a canal may be narrow at its bottom half and diverge rapidly in the top half or it may be too oval shaped. The preformed post which is of the same diameter throughout can not accommodate these situations. When utilizing a cast post, root preparation is done by drilling to remove undercuts and obtain slight divergence from the bottom upward. The cast post technique takes an impression of a prepared root canal space. In indirect methods, an impression of the root is taken with a dental impression material. In direct methods, an acrylic pattern of the prepared root and the desired shape above the gums is achieved in the mouth. Laboratory procedures which include casting in a lost wax technique are then necessary to construct the cast post. There are many problems which are encountered when utilizing casts posts. The problems include: An increased chance of root fracture. The cast post is expensive. There is an increased possibility of root perforation. The cast post may not provide good resistance to rotational forces.

All posts need to provide venting of cement as a post is placed. A cast post is very precise fitting so it is difficult for cement to vent, lateral forces can fracture the root and/or the post will not be fully seated as excess cement remains in the bottom. In addition, any bubbles or inaccuracies from the casting process can cause a poor fit and root fracture. Cast posts dramatically increases cost as compared to preformed posts because there are laboratory fees and increased time required to treat the patient. For a cast post, an appointment is needed for an impression in addition to an appointment for post placement. The patient cost of a cast post is double the cost of a preformed post. The doctors laboratory cost may be five to ten times the cost to buy a preformed post.

Preparation of a root canal space must be free of any undercuts or removal of a cast post in its plastic or wax phase of construction will be impossible. It is often difficult to attain this as root canals tend to be complex systems of lateral canals, ribbon shapes, multiple canals, etc. Often, excessive drilling is done which removes important tooth structure and leads to a weaker root and increased chance of root fracture or perforation.

It has been proposed in U.S. Pat. Nos. 4,480,997; 4,490,116 and Re. 31,948 to utilize a threaded dental post which is introduced into the bore of a tooth stub by being rotated to thread the post into position. The dental post includes a stem portion having a slot extending through the stem thickness and along its length which renders the stem being formed of two legs each having its outside surface threaded. The outside surface of the legs intimately contact the walls of the bore so that the threads on the legs can engage the walls. In addition, a spring-like connection for the two legs is provided so that a radial outward spring force is applied to the legs to force them against the bore walls. These dental posts are undesirable since a rotational force must be applied to the post to position it properly into the bore. This positioning process is undesirable since it is time consuming and causes the patient discomfort. In addition, the possibility exists that the post will be threaded too far into the tooth stub which will result in fracture of the tooth stub. Furthermore, the radially outward forces of the legs on the tooth stub can result in fracture of the tooth stub over time.

U.S. Pat. No. 1,534,409 discloses a two legged post having corrugated surfaces which fit into a root canal having generally parallel walls. This surface design materially reduces the post surface area which contacts the canal walls and thus post retention relies primarily upon cement adhesive strength.

Accordingly, it would be desirable to provide a dental post which can be inserted into the bore of a tooth stub while eliminating the need for sole reliance upon lateral stress forces with the canal wall or upon the adhesive strength of an adhesive. In addition, it would be desirable to provide a dental post which distributes force on the tooth so that it is not concentrated on the post or on a pin used in conjunction with the post. Furthermore, it would be desirable to provide a system for utilizing such a dental post which facilitates the placement of a core and a crown.

SUMMARY OF THE INVENTION

This invention provides a dental post having a stem section formed integrally with a flange such as a disk which is positioned on the top surface of a tooth stub. The disk position of the post can include pins formed integrally therewith or can be provided with holes through which pins can be inserted. The disk serves to distribute force on the tooth so that the force is not concentrated on the post stem or on one or more pins unconnected to the post. The pins, when used, can be positioned parallel with the stem or at an angle to the stem. A dental adhesive or bonding material is place in the tooth bore prior to placing the post within the bore.

BRIEF DESCRIPTION OF THE DRAWINGS

FIG. 4 is a perspective view of an alternative dental post of this invention.

FIG. 5 is a perspective view of an alternative dental post of this invention.

FIG. 6 is a perspective view of an alternative dental post of this invention.

DESCRIPTION OF SPECIFIC EMBODIMENTS

The dental post of this invention includes a stem which extends into a tooth bore and a flange such as a disk formed integrally with the stem. The disk is positioned at an intermediate position along the post so that the stem extends both above and below the disk. The top and bottom stem sections may be tapered, round, square, triangular, rectangular, hexagonal, etc. and may have a through splint, be grooved, roughened, tapered screw threaded, etc. or combinations of these. The disk can have pins formed integrally with the disk or holes can be provided through which pins can be inserted. The pins, once inserted through the disk holes can be bent at an angle thereby to assist in retaining the post and core materials in place. Filler material or a fitting core and a crown then are placed on the post positioned in the tooth stub. The disk is positioned on the tooth stub surface or in an indentation on the tooth stub surface.

The disk serves to distribute normal forces on the tooth away from the stem and away from the pins used in conjunction with the post. The disk and pins provide increased retention and antirotation to the post.

Figure 1:
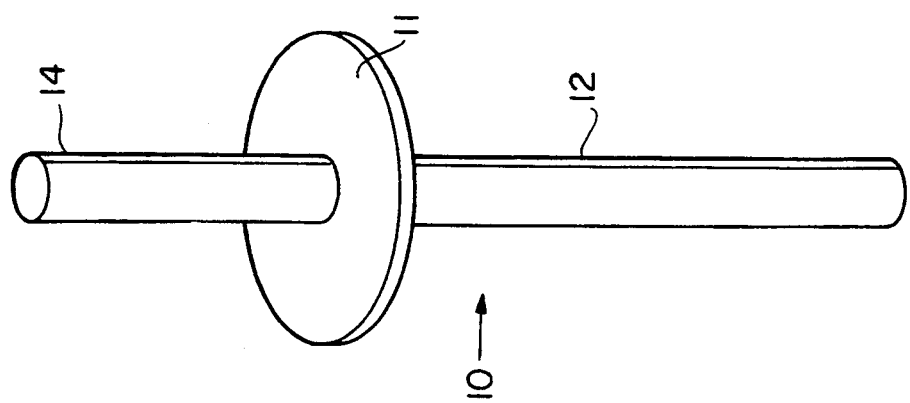
FIG. 1 is a perspective view of a dental post of this invention.

Referring to FIG. 1, the dental post 10 formed from any suitable dental material includes a disk 11, a bottom section 12 and a stem section 14.

Figure 2:
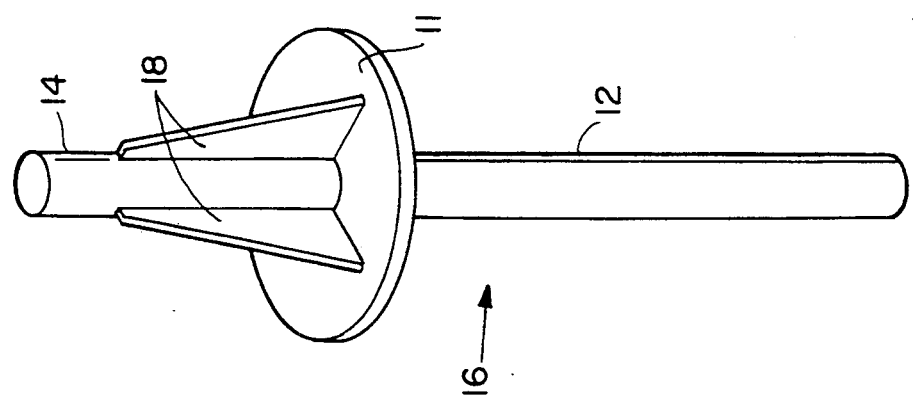
FIG. 2 is a perspective view of an alternative dental post of this invention.

Referring to FIG. 2, the post 16 includes a disk 11, a bottom section 12, a stem section 14 and stem supports 18 bonded to disk 11 and stem section 14.

Figure 3:
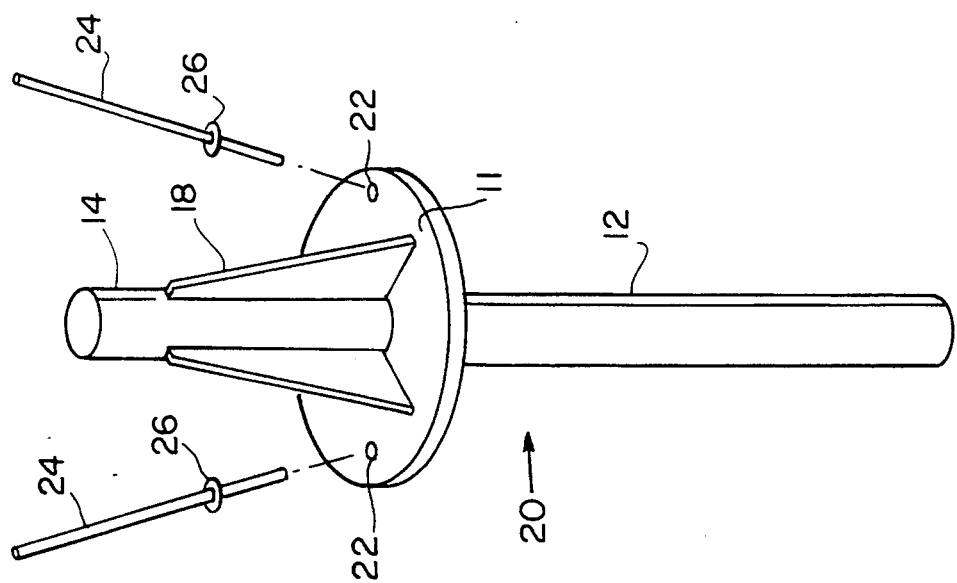
FIG. 3 is a perspective view of an alternative dental post of this invention.

Referring to FIG. 3 and 4, the dental post 20 includes stem section 14, bottom section 12, disk 11 through holes 22 and pins 24. The pins 24 have stops 26, which may be eliminated, to limit the length of their insertion through holes 22. The pins are inserted at an angle toward the center of the tooth stub 28 so as to prevent their breakthrough, from the tooth stub surfaces 30 and provide mechanical retention to the post. As shown if FIG. 5, more that one through hole 22 can be utilized to accommodate pins 24. The pins 24, after insertion into holes 22 are bent toward stem section 14 to impede the removal from holes 22 and supply retention to core build up materials. The pins 24 may be cut off if a custom core is to be placed. As shown in FIG. 6, the post 32 can have a bottom section formed of two spaced apart legs 34 which can have threads so that the post 32 can be screwed into a root canal.

The dental post can be made of a variety of sizes. For example, a dental post can extend about 3 to 18 mm into the root and 1 to 7 mm above the root. A typical dental post diameter can vary between about 0.2 mm and 2 mm. The disk diameter can vary between 1 to 20 mm. It is to be understood that these dimensions are exemplary and will vary with the need of the patient.

Figure 9:
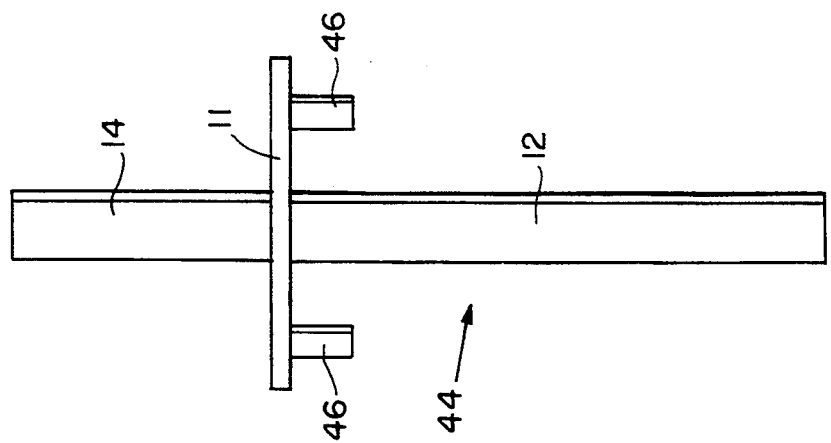
FIG. 9 is a perspective view of an alternative dental post of this invention.
Figure 7:
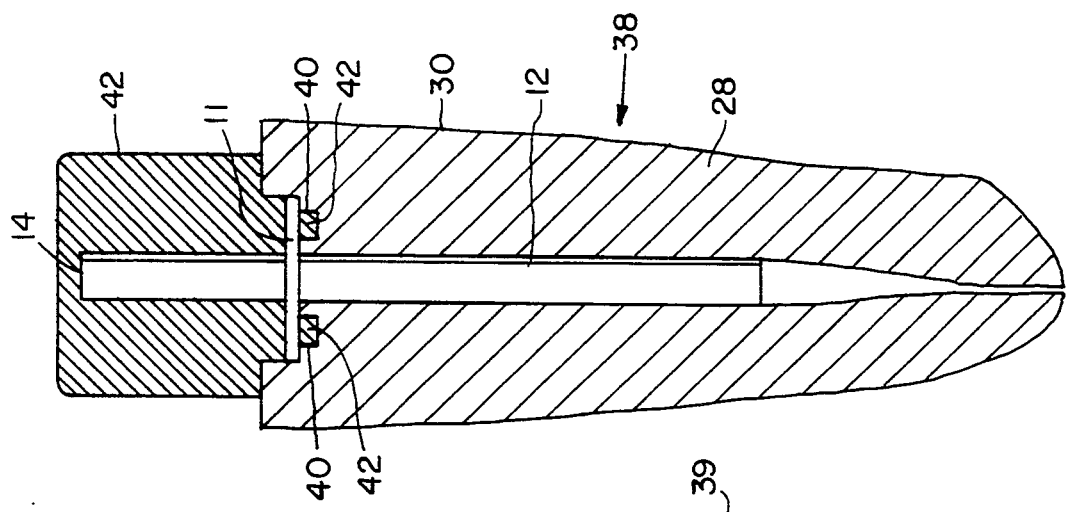
FIG. 7 is a perspective view of an alternative dental post of this invention.
Figure 8:
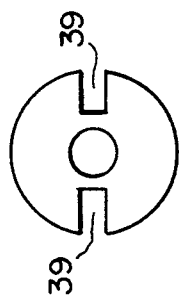
FIG. 8 is a top view of the post for FIG. 7.

As shown in FIGS. 7 and 8, the post 38 can have a disk 11 with holes 39 which permit insertion of a bur to form holes 40 in tooth stub 28 so that filling material 42 can extend into tooth stub 28. As shown in FIG. 9, the post 44 includes a stem section 14, a bottom section 12, a disk 11 and preformed pins 46 which are shaped to fit into holes of a tooth stub (not shown) which can be formed with a conventional bur or drill.

Figure 10:
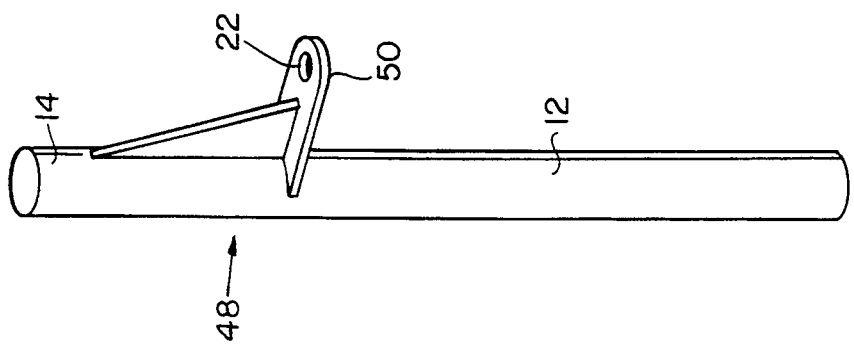
FIG. 10 is a perspective view of an alternative dental post of this invention.

Referring to FIG. 10, the post 48 can comprise a disk 50 which is not circular and which has a hole 22 for insertion of a pin (not shown). The post 48 includes a stem section 14 and bottom section 12.

Figure 11F:
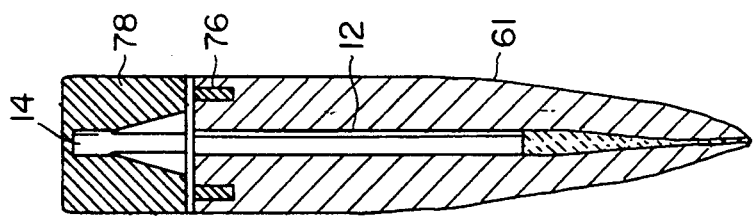
FIGS. 11a-f are cross-sectional views illustrating the installation of a dental post of this invention.
Figure 11E:
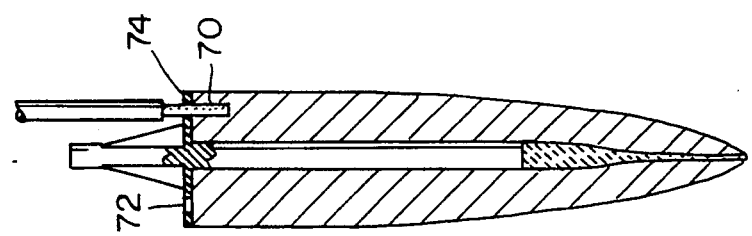
Figure 11D:
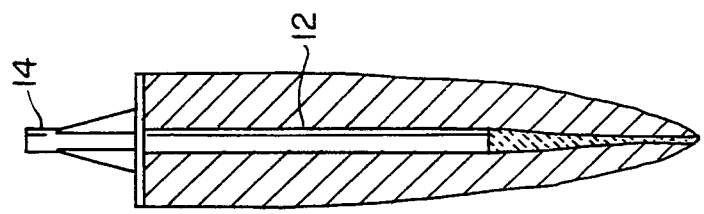
Figure 11C:
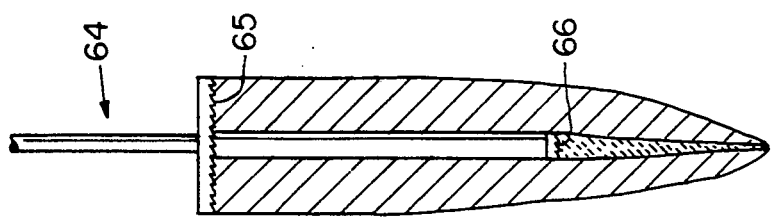
Figure 11B:
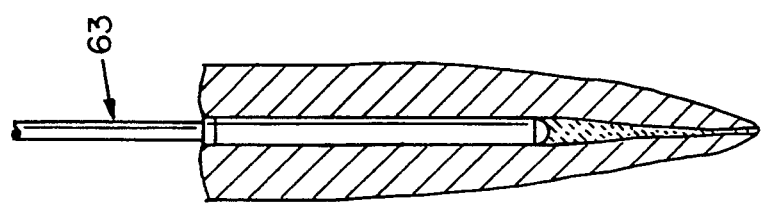
Figure 11A:
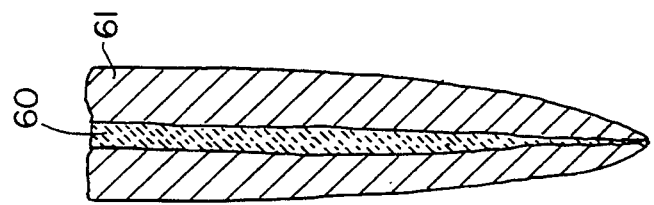

Referring to FIGS. 11a to 11f, the use of the system of this invention is illustrated. As shown in FIG. 11a, an initial tooth bore 60 is formed with a conventional reamer and filled with a conventional filling material such as a gutta percha based material in tooth stub 61. In a second step as shown in FIG. 11b, a bur 63 is used to shape the bore. The final bore shape is formed with bur 64 having a cutting surface 65 and 66 as shown in FIG. 11c. The use of cutting surface 66 is optional. The bottom surface 66 of the bur 64 is flat thereby forming a flat surface on the remaining filling material in the bottom of the tooth bore. As shown in FIG. 11e, bur 70 is then inserted into holes 72 of disk 74 as shown in FIG. 11f to form holes in tooth stub 61 so that the legs 75 of core 87 can be positioned in the tooth stub 61.

I claim:

1. A dental post for insertion into a bore of a tooth stub which comprises:
   a stem comprising a bottom stem section and a top stem section,
   a flange secured to an intermediate vertical position on said stem, such that when said post is positioned into said bore, said bottom stem section extends into said bore, said flange rests on a top surface of said tooth stub and said top stem section extends away from the top surface of said tooth stub,
   said flange including at least one through hole surrounded by material forming said flange,
   and a pin extending through said at least one through hole extending at an angle relative to said stem.

2. The post of claim 1 wherein said flange extends about a portion of the periphery of said stem.

3. The dental post of claim 2 including at least one support means connecting said top stem section and said flange.

4. The dental post of claim 2 wherein said flange includes at least one through hole.

5. The dental post of claim 2 including at least one support means connecting said top section and said flange and wherein said flange includes at least one through hole.

6. The post of claim 1 wherein said flange extends about the entire periphery of said stem.

7. The dental post of claim 6 including at least one support means connecting said top stem section and said flange.

8. The dental post of claim 6 wherein said flange includes at least one through hole.

9. The dental post of claim 6 including at least one support means connecting said top section and said flange and wherein said flange includes at least one through hole.

10. The dental post of claim 1 including at least one support means connecting said top stem section and said flange.

11. The dental post of claim 1 wherein said flange includes at least one through hole.

12. The dental post of claim 1 including at least one support means connecting said top section and said flange and wherein said flange includes at least one through hole.

13. The dental post of claim 1 having a plurality of said pins.

* * * * *